United States Patent [19]

Son et al.

[11] Patent Number: 5,053,505
[45] Date of Patent: Oct. 1, 1991

[54] PROCESS FOR THE MANUFACTURE OF A TRI-SUBSTITUTED TRIAZINE STABILIZER

[75] Inventors: Pyong N. Son, Akron; John T. Lai, Broadview Heights; Ronald M. Kovach, Avon Lake, all of Ohio

[73] Assignee: The B. F. Goodrich Company, Akron, Ohio

[21] Appl. No.: 526,194

[22] Filed: May 21, 1990

[51] Int. Cl.$^5$ .................. C07D 243/08; C07D 403/04; C07D 403/14
[52] U.S. Cl. ..................................... 540/575; 544/198; 544/215
[58] Field of Search ................. 540/575; 544/215, 198

[56] References Cited

U.S. PATENT DOCUMENTS

| | | | |
|---|---|---|---|
| 4,190,571 | 2/1980 | Lai et al. | 524/100 |
| 4,480,092 | 10/1984 | Lai et al. | 524/100 |
| 4,547,538 | 10/1985 | Lai et al. | 524/100 |
| 4,629,752 | 12/1986 | Layer et al. | 524/100 |

*Primary Examiner*—Johann Richter
*Attorney, Agent, or Firm*—Alfred D. Lobo

[57] ABSTRACT

A staged process is disclosed for forming a tri-substituted triazine ring in which the substituents are cyclic amines referred to as hindered amines. A prior art process for making such amines in a reaction mixture of aqueous and organic phases has been modified to produce a stabilizer with desirable whiteness, at the same time avoiding the loss of the cyclic amine reactant which is water-soluble. Conversion of the amine to yield at least 90% of the tri-substituted product having at least 90% purity allows the reaction to be commercially significant despite the high cost of the reactants. The staged process is preferably conducted in two sequences in two reactors, with an intermediate step in which the aqueous saline and basic solution from the first sequence is withdrawn. In the first sequence, a mono-chloro intermediate ("MCI") is formed at ambient temperature, but below 100° C. to yield a colored solution. Flowing only the organic phase to the second reactor which must be pressurized, allows use of an economical reactor. In the second sequence, preferably in a separate reaction zone, reacting 3 moles of MCI with no more than 3.5 moles of a third amine, yields the tri-substituted product which is formed at below 200° C. but in excess of 125° C. Only a small portion of the molar excess of amine used in the second sequence need be discarded. The time required to run the reaction in two stages is less than required to run it in a single sequence. Further saving in time is effected by using a phase transfer catalyst.

23 Claims, 2 Drawing Sheets

PROCESS FOR THE MANUFACTURE OF A TRI-SUBSTITUTED TRIAZINE STABILIZER

BACKGROUND OF THE INVENTION

It is self-evident that a compound cannot be marketed succesfully if it cannot be produced economically. In addition to the cost of raw materials for making the compound, its cost of production depends upon numerous other factors including the purity required, the color, or lack thereof, demanded for the compound, the time required to make it, and of course, the amount of by-products and scrap which result. The weighting of each of the foregoing factors looms the larger with the increasing cost of the raw materials, the inflexibility of the conditions of reaction, and the exigency of the color qualifications, all of which lead to high scrap production in an unforgiving process. The tri-substitution of a trihalo-s-triazine, specifically cyanuric chloride, with a cyclic amine substituent is such a process.

The cyclic amine substituent is preferably derived from a piperidine, piperazine or piperazin-2-one, hexahydro-2$\underline{H}$H-1,4-diazepine or hexahydro-2$\underline{H}$-1,4-diazepin-2-one, any of which is an expensive material. Since, for economic reasons, essentially no unreacted cyanuric chloride may remain, preferably none which is not tri-substituted, or otherwise reacted to form unwanted byproducts, there is no practical alternative to using an excess of the amine, the bigger the excess, the more cyanuric chloride being tri-substituted. Except that separating and recovering the excess unreacted amine from the reaction mass is difficult and uneconomical. The result is that excess amine is discarded with other byproducts and wasted. It is this process to which this invention is directed.

The concept of structurally manipulating the architecture of multi-ringed hindered amine cyclic compounds along with the linking groups which link them to a triazine ring, has been at the forefront of the enormous effort to stabilize synthetic resinous materials against degradation by oxygen, heat and actinic radiation, particularly ultraviolet light. Among the most successful of the architectures are one or more triazine rings linked through a nitrogen atom, or a linking group containing a nitrogen atom, to a piperidine, piperazine, piperazin-2-one, hexahydro-2$\underline{H}$-1,4-diazepine, or hexahydro-2$\underline{H}$-1,4-diazepin-2-one ring which has multiple substituents on the ring carbon atoms. Each of the foregoing cyclic amines is referred to by the acronym "PSP", for brevity, because they are polysubstituted.

Substituents and tri-substituted triazines are disclosed in U.S. Pat. Nos. 4,190,571, 4,480,092, and 4,547,538 to Lai et al; and, U.S. Pat. No. 4,629,752 to Layer et al; all in class 524/subclass 100, the disclosures of which are incorporated by reference thereto as if fully set forth herein.

In example 3 of the '538 patent, cyanuric chloride is mono-substituted with a piperazinyl substituent (referred to as a piperazinyl-triazine or "PIP-T" for brevity) to form 2,4-dichloro-6-[1-methylpropyl[2-(3,3,5,5-tetramethyl-2-oxo-1-piperazinyl)ethyl]amino]-1,3,5-triazine (m p 93°–95° C.) by reacting equimolar amounts of 1-[2-(2-butylamino)ethyl]-3,3,5,5-tetramethyl-piperazin-2-one (a specific PSP referred to as PSP$_1$) and cyanuric chloride in acetone and water, in the presence of sodium carbonate.

A second PSP$_1$ may be added if a slight excess over 2 moles of the PSP$_1$ are reacted with 1 mole of cyanuric chloride, but the reaction must be completed under reflux conditions to obtain more than 50% yield (lb recovered/lb theoretically produced).

Under such reflux conditions, the reaction for the substitution of a third PSP$_1$ on the triazine ring, in aqueous solution, produces less than 50% yield. Recognizing the necessity of a high temperature to make the substitution on the third C atom of the triazine ring, the patent teaches carrying out the reaction in an inert organic solvent with a suitably high boiling point, for example toluene or xylene.

With another PSP, referred to as PSP$_4$, example 6 of the '538 patent illustrates how easily the reaction of equimolar amounts of cyanuric chloride and 1-[2-(2-propylamino)ethyl]3,3,5,5-tetramethyl-piperazin-2-one in solution in toluene proceeds. The reaction is run at 10° C., then a molar excess of 20% NaOH solution is stirred with the reaction mass overnight, to produce the mono-substituted triazine. Though the color of the product was good, the time required at low temperature is so long that it became necessary to run the reaction at higher temperature and elevated pressure. This shortened the time of reaction but increased the by-product formation and degraded the color. The product collected was 70 g (m p 118°–121° C.), which represents a yield of about 55.6%. Since such a yield precludes the commercial preparation of the compound, a more economic approach was required.

Then to introduce the second and third substituents, as described in example 7, the mono-substituted triazine ring was reacted with a PSP in toluene solution at about 200° C. for 10 hr. Nothing is stated about the color of the product obtained, or its yield, or the amount of the mono-substituted reactant which remained unconverted.

Specifically, the PIP-T was tri-substituted PSP$_4$, made in stages when 1 mole of cyanuric chloride was first reacted with 2 moles of the PSP$_4$, with the addition of 2 moles of aqueous NaOH at a temperature below 35° C. The mono-chloro intermediate ("MCI"), namely the triazine di-substituted with two PSP$_4$s, (m p 126°–130° C.), was formed. It is then stated that an additional (third) mole of the PSP$_4$ is then reacted with a mole of cyanuric chloride. Since no molar excess of PSP$_4$ is stated to have been used, the yield of product could not have been more than 90% even over a long period of time which would not be tolerable if the color of the product is to be white. The product is progressively colored with increasing temperature and longer time. The term "molar excess" is used herein relative to the trihalo-s-triazine used. Tri-substitution requires 3 moles of amine and 3 moles of base to neutralize the HCl formed; if 3.5 moles of amine are used, the molar excess of amine is 50%, and if 3.2 moles of base are used, the molar excess of base is 20%.

No conditions are stated for making the tri-substituted PIP-T, but referring to example 4 of the patent, it is seen that making a tri-substituted PIP-T in toluene, with PSP$_3$ substituents, requires the reaction to be carried out at 200° C. for 10 hr. That tri-substituted product (m p 179°–180° C.) was straw colored. When recrystallized from toluene, the product was off-white. At or above 200° C., the evidence is that a desirably white product is not formed. There is no indication as to how much, if any, of the amine reactant was converted to the amine hydrochloride at the elevated temperature used.

It will be appreciated that amine converted to the hydrochloride is unreactive and will not be a substituent.

It will also be appreciated that when there is a "color problem" even on a laboratory scale, the problem is magnified when the reaction is carried out on a commercial scale.

The problem of color is serious because stabilizer with a "color problem" is essentially unmarketable. The seriousness of the problem becomes the more economically debilitating because it has been found that in many instances, with a wide variety of PSPs which have been used to make the tri-substituted PIP-T, the color cannot be expunged even by multiple recrystallizations. This problem will be addressed in this specification, with specific regard to those PSPs which must be used in relatively large molar excess, namely about a 50% excess, relative to 1 mole of cyanuric chloride, to produce an economically acceptable yield of tri-substituted PIP-T. Despite such large excess of PSP, the tri-substituted PIP-T produced is typically "colored" because the reaction must be carried out at relatively high temperature, and typically, for more than 10 hr. The color generated may be due to a wide variety of factors, but a major one is that the combination of high temperature and long time is prone to yield difficult-to-separate by-products which are in large part responsible for poor color.

The approach to the twin problems of yield and color was determined by trying to best cope with them, rather than to find either a perfect or an all-encompassing solution, since it became evident that, for tri-substitution of cyanuric chloride, the presence of the relatively large molar excess of about 3.5:1 (moles of amine : cyanuric chloride), and a temperature in excess of 150° C., preferably more than 200° C., both appeared to be necessary to provide a practical, economic process. Further, it was to be expected that tri-substitution of cyanuric chloride with some amines would result in either more, or less, color than with other amines or triazines; and, that few, if any, amines would lend themselves to being recovered from the reaction mass economically, irrespective of the particular molar excess in which they were used.

The problems relating to manufacturing the trisubstituted PIP-T product economically are exacerbated by the fact that the PSP amines are soluble in water, and the reaction for making any PSP substitution, particularly the last, does not proceed satisfactorily in the aqueous phase. Moreover, excess amine in aqueous solution is so difficult to recover that, despite its high cost, it is presently more economical to discard it.

It happened that, unlike a cyclic amine (PSP), the solubility of MCI in water is low, but it was nevertheless essential that the loss of MCI in the aqueous phase be minimized. It was therefore advantageous to find that greater amounts of MCI migrated to the organic phase when the aqueous solution was both saline and highly basic, than when it is neutral (distilled water), and even more so when the solution was not hot. Stated differently, less of the required excess of amine went into solution in the aqueous phase when it was cold, saline and pH 14, than if the aqueous phase was not saline, was not basic, plain water.

Still further, because it was discovered that the reaction proceeded faster in the alkylbenzene phase, it became possible to use a phase transfer catalyst to accelerate the substitution of the PSPs, particularly the third (and last) substituent.

Finally, though one would reasonably expect the purity of the amine and triazine reactants to affect the color and yield of tri-substituted product, it was not reasonable to expect that the concentration of the base might have a large effect on both color and yield of product, particularly when the last substituent is to be substituted. Since each mole of HCl formed must be neutralized during the reaction, at least an equimolar amount of base must be used. Further, since the presence of some water facilitates the substitution of PSPs, typically, an aqueous solution of an alkali metal hydroxide, or an alkaline earth metal carbonate, is used. Because aqueous base is commercially economical to use, a large amount of water, far in excess of that required to initiate and propagate the reaction, is included in the reaction mass. Since the cyclic amine is soluble in water, one would expect to use as concentrated a base as practical, to avoid loss of amine during work-up of the reaction mass. Except that the more concentrated the base, the worse the color of the PIP-T product. The more dilute the base, the longer the time for reaction at the high temperature required to make the trisubstitution; and more difficult to recover both product and excess amine; and, the larger the reactor necessary.

Since it is critical that the recovered trisubstituted product, upon work-up or recrystallization, be desirably white, it was not obvious how to arrive at the appropriate range of requirements for the overall reaction, especially the aqueous phase. The color requirement for acceptable recrystallized product is defined by melting a small quantity of the crystals and measuring the melt color with a spectrophotometer; when expressed as melt absorptivity mL/gm.cm under nitrogen, acceptable color is defined as being less than 3.5 mL/gm.cm.

With the foregoing strictures it was decided to compartmentalize (or stage) the process steps. Such staging into first and second sequences of substitution was deemed to help control each step in a sequence more precisely, to minimize the formation of color-forming impurities in the first sequence, and in the second sequence, to manipulate the formation of the trisubstituted PIP-T product with desirable whiteness by minimizing the time of exposure to the required high temperature, yet to maximize yield, thus reactor productivity (weight of product per unit volume of reactor, per unit time).

SUMMARY OF THE INVENTION

It has been discovered that by dividing a process for forming a tri-substituted triazine ring into a first sequence in which a mono-chloro intermediate ("MCI") is formed in a colored solution at low temperature, and a second sequence, preferably in a separate reaction zone, in which the trisubstituted product is formed at a higher temperature, both the whiteness and the yield requirements for the trisubstituted product are met. Moreover, only a relatively small portion of the molar excess of amine used in the second sequence need be discarded; further, that such molar excess was less than 50% of the one (last) mole required to provide the third (and last) substituent; and that, since the starting material in the second sequence is the MCI, the time required to form the MCI is avoided in the second sequence (because it was already made in the first sequence).

It is therefore a general object of this invention to provide a process which allows optimum reactor productivity while producing desirably white, tri-substituted triazine, having an amine substituent on each carbon atom; further, the product is produced with an yield in excess of 90% using less than a 50% excess of one mole of the amine to be substituted at the third (and last) substitutable carbon atom on the triazine ring, despite the reaction in the second sequence being carried out at below 200° C. but in excess of 125° C.

It is also a general object of this invention to provide first and second sequences in a staged process for tri-substitution of a triazine ring with a cyclic amine, the second sequence of which process comprises making the third amine substitution in less time than is required to add three amine substituents to cyanuric chloride in a single sequence, under otherwise identical temperature and pressure conditions without sacrificing yield, and with better whiteness; and, recovering the desired tri-substituted product from the reaction mass.

It has specifically been discovered that the presence of a large amount of water in the reaction mass, not only is wasteful of necessary excess amine which is water-soluble, and which must also be added in molar excess (that is, on a 2.5 molar basis relative to cyanuric chloride) to achieve an economically acceptable yield of product and a practical rate of reaction, but requires a larger pressure reactor; further, excess water deleteriously affects yield and whiteness (lack of color, or simply "color") of the tri-substituted product.

It is therefore a specific object of this invention to provide, in a process for substituting first and second amine PSP substituents in a triazine ring in a first sequence, and the third substituent on the ring in a second sequence, the improvement comprising, maintaining the presence of a controlled amount of water in aqueous base in each sequence. Preferably the amount is introduced in a 15%–50% aqueous solution of base, more preferably in a 20%–35% aqueous solution of base. The amount of base used is present in no more than a 25% molar excess.

It is another specific object of this invention to provide a controlled concentration of salt in a saline, basic, solution generated by reaction of the aqueous base with HCl generated by substitution of Cl atoms on the triazine ring, to force excess amine out of the saline (pH 14) aqueous solution (lower layer), and into the organic (alkylbenzene) upper layer; to provide an intermediate step between the first and second reaction zones, in which step the aqueous layer is withdrawn to decrease the volume of liquid being flowed to the second reaction zone; and, to minimize the contribution of the saline solution to dark color. The upper layer, depleted of base and water, may then be reacted with a controlled excess of amine and fresh aqueous base which excess is determined more accurately than if the amount and concentration of base in aqueous saline solution was transferred from the first reaction zone.

It has also been discovered that substitution particularly of the third amine substituent in the second sequence of the process can be accelerated by the addition of a phase transfer catalyst, all other process conditions being kept the same.

It is therefore also an object of this invention to minimize the exposure of tri-substituted product to high temperature by adding the last substituent in the second sequence; and, to save an additional amount of time for the reaction in the second sequence, by using a phase transfer catalyst to accelerate substitution of the third substituent, without sacrificing either acceptably white color or yield.

It is a specific object of this invention to make a commercial grade, hindered amine-containing triazine stabilizer, comprising, in a first sequence, preparing a precursor MCI (cyanuric chloride di-substituted with PSP amine substituents) having the desired first and second PSP substituents, which may be the same or different, at a temperature from about ambient to below 100° C.; then, in a second sequence, reacting 3 moles of MCI with no more than 3.5 moles of a third amine, which may be the same or different from either one, or both, of the amine(s) used to provide the first two amine (PSP) substituents, at a temperature above 125° C., preferably in the range from about 150° C. but below 200° C. so as to produce a tri-substituted product in excess of 90% yield, yet having desirable lack of color.

It is a specific object of this invention to provide a process for manufacturing a tri-substituted triazine compound having a single triazine ring, each carbon atom of each ring being connected through a tertiary N atom to a hindered amine substituent which may be the same or different on each C atom of the ring, the process comprising, in a first sequence, (a) dissolving a chosen molar quantity of cyanuric chloride in an inert organic solvent therefor;

(b) reacting each mole of cyanuric chloride with more than 2 but less than 3 moles of amine substituent(s) at a temperature below about 100° C. for a time sufficient to convert at least 95% by weight, preferably essentially all, of the cyanuric chloride so as to provide a colored reaction mixture in which is dissolved MCI which in solid form, is generally straw-colored or brown, and not free from color;

(c) adding at least 2 moles of an aqueous inorganic base in a concentration of less than 50% base to form an aqueous saline solution; and, in an intermediate step, (d) separating the aqueous saline solution having a pH 14 from the organic phase; and in a second sequence, (e) reacting 3 moles of MCI with no more than 3.5 moles of a third amine at a temperature in the range from above 125° C. but below 200° C. and autogenous pressure, in the presence of an additional amount of said aqueous solution of inorganic base having a concentration of from about 15% to 50%, in an amount sufficient to neutralize acid formed during the reaction, but no more than a 25% molar excess of base, for a time sufficient to convert at least 90% by weight of the disubstituted triazine to a tri-substituted product; and, (f) recovering a tri-substituted product having a purity in excess of 95% with a yield in excess of 90%, which product upon work-up or recrystallization is white or off-white in color.

It is a specific object of this invention, to use no more that 3.5 moles of the amine 3 moles of MCI in step (e) to provide a conversion of at least 95% of the MCI (lb converted/ lb charged) to the tri-substituted triazine. dr

BRIEF DESCRIPTION OF THE DRAWINGS

The foregoing and other objects and advantages of our invention will appear more fully from the following detailed description, made in connection with the accompanying diagrams of flowsheets wherein.

DETAILED DESCRIPTION OF THE INVENTION

Figure 1:
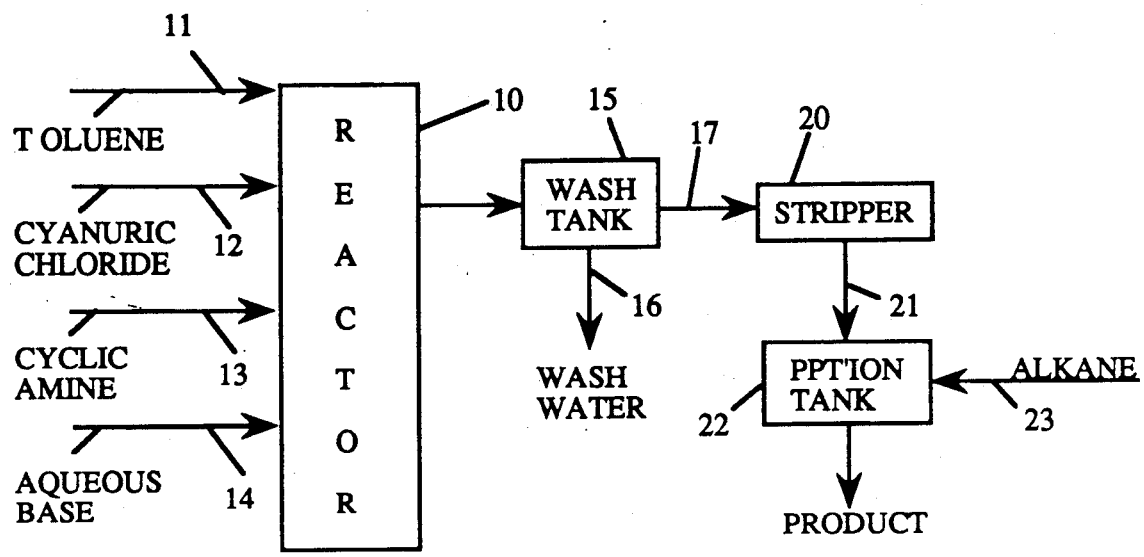
FIG. 1 is a block diagram schematically representing a flowsheet for a prior art process for trisubstituting cyanuric chloride with a cyclic amine.

The substituted triazine is represented by the structure

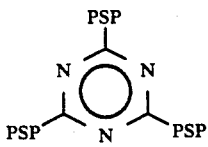

wherein PSP represents a substituent derived from a cyclic amine represented by a structure selected from the group consisting of

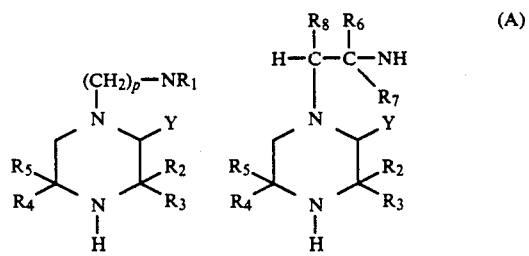

wherein,

Y represents H or =O, and m is 1 or 2;

$R_1$ represents $C_1-C_{24}$ alkyl, $C_5-C_{12}$ cycloalkyl, $C_7-C_{20}$ aralkyl or alkaryl, $C_1-C_{24}$ azaalkyl, $C_6-C_{20}$ azacycloalkyl;

$R_2$, $R_3$, $R_4$, and $R_5$ independently represent $C_1-C_{24}$ alkyl;

$R_6$, and $R_7$ independently represent $C_1-C_{24}$ alkyl and polymethylene having from 4 to 7 C atoms which are cyclizable;

p represents an integer in the range from 2 to about 10; and, $R_8$ represents H, $C_1-C_6$ alkyl and phenyl; and,

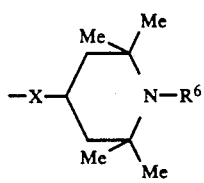

wherein,

Me = methyl $R^6$ represents hydrogen, oxyl oxygen, $C_1-C_{12}$ alkyl, $C_3-C_7$ alkenyl, $C_1-C_{18}$ alkoxy, $C_7-C_{11}$ phenylalkyl, cyanomethyl, $C_2-C_{18}$ alkanoyl, $C_3-C_{18}$ alkenoyl, or a group —CON($R^7$)($R^8$) in which $R^7$ is $C_1-C_{12}$ alkyl, allyl, cyclohexyl, benzyl, phenyl, or $C_7-C_{12}$ alkylphenyl, and $R^8$ is hydrogen, $C_1-C_{12}$ alkyl, allyl or benzyl, or $R^7$ or $R^8$ together with the N atom to which they are attached, form a 5-membered ring or 6-membered heterocyclic ring; and, X is a divalent group of the formula —O—, —NH—CH$_2$—CH$_2$—, —NH—(CH$_2$)$_2$—O— and the like; or a monovalent group of the formula RNH where R is $C_1-C_{18}$ alkyl or cycloalkyl; and,

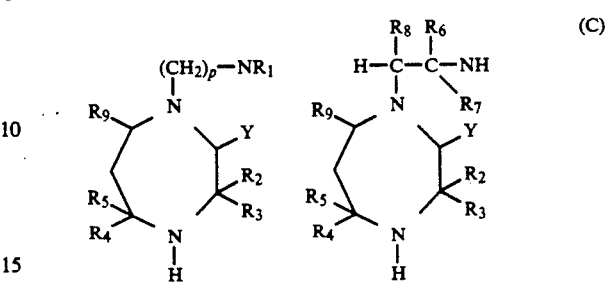

wherein, the substituents have the same connotation as given hereinabove, and, $R_9$ is $C_1-C_{12}$ alkyl.

A particular PIP-T which is tri-substituted with a particular PSP amine reactant, 1-[3-(cyclohexylamino)-propyl]-3,3,5,5-tetramethyl-piperazin-2-one, familiarly referred to as "CHP" for brevity is represented as follows:

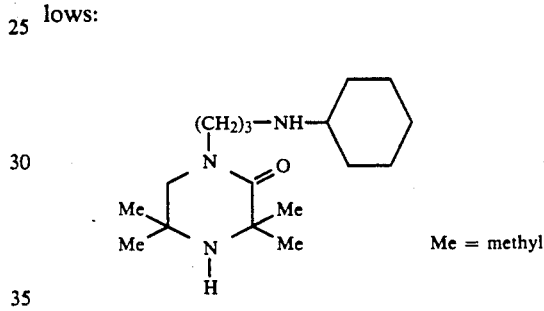

Me = methyl

Particular tri-substituted triazines are derived from the following PSP piperazin-2-one and piperazine substituents:

1-[3-(isopropylamino)propyl]-3,3,5,5-tetramethyl-piperazin-2-one;

1-[2-(isopropylamino)ethyl]-3,3,5,5-tetramethyl-piperazin-2-one;

1-[2-(butylamino)ethyl]-3,3,5,5-tetramethyl-piperazin-2-one; and,

1-[2-(cyclohexylamino)ethyl]-3,3,5,5-tetramethyl-piperazin-2-one;

1-[3-(isopropylamino)propyl]-3,3,5,5-tetramethyl-piperazine;

1-[2-(isopropylamino)ethyl]-3,3,5,5-tetramethyl-piperazine;

1-[2-(butylamino)ethyl]-3,3,5,5-tetramethyl-piperazine; and,

1-[2-(cyclohexylamino)ethyl]-3,3,5,5-tetramethyl-piperazine; inter alia.

Particular tri-substituted triazines are derived from the following PSP diazepin-2-one and diazepine substituents:

1-[3-(isopropylamino)propyl]-3,3,5,5-tetramethyl-hexahydro-2H-1,4-diazepin-2-one;

1-[2-(isopropylamino)ethyl]-3,3,5,5-tetramethyl-hexahydro-2H-1,4-diazepin-2-one;

1-[2-(butylamino)ethyl]-3,3,5,5-tetramethyl-hexahydro-2H-1,4-diazepin-2-one; and, 1-[2-(cyclohexylamino)ethyl]-3,3,5,5-tetramethyl-hexahydro-2H-1,4-diazepine;

1-[3-(isopropylamino)propyl]-3,3,5,5-tetramethyl-hexahydo-2H-1,4-diazepine;

1-[2-(isopropylamino)ethyl]-3,3,5,5-tetramethyl-hexahydro-2H-1,4-diazepine;

1-[2-(butylamino)ethyl]-3,3,5,5-tetramethyl-hexahydro-2H-1,4-diazepine; and,

1-[2-(cyclohexylamino)ethyl]-3,3,5,5-tetramethyl-hexahydro-2H-1,4-diazepine; inter alia.

In a particularly preferred embodiment, the MCI is produced in a first sequence in a first reactor which is fitted with appropriate agitating and heating means, such as a double-bladed propeller, bayonet heat exchanger or internal heating and cooling coils, and a heating or cooling jacket. For each mole of cyanuric chloride charged to the reactor, is charged from 2 to 3 moles, preferably from about 2.2 to about 2.75 moles of amine to be substituted (PSP); from 2 to 3 moles, preferably from about 2.2 to about 2.75 moles of 30% aqueous NaOH solution, and enough alkylbenzene solvent to maintain the solids in solution.

Neither the amount nor the concentration of aqueous NaOH solution used in the first sequence is narrowly critical, particularly if the aqueous saline layer is to be withdrawn in an intermediate step, but a sufficient excess is used, calculated to provide a saline solution containing at least 25% NaCl when production of MCI is completed.

Typically there is in the first reactor at least 2.5 volumes of toluene for each volume of water introduced with the aqueous inorganic base. The temperature of the reaction mass is raised to about 60° C. and the reaction allowed to proceed until at least 95% of the cyanuric chloride is converted and the yield to MCI is at least 90%.

In an intermediate step, the contents of the reactor are then dumped to a decantation tank where the reaction mass is allowed to settle and the basic NaCl solution is drawn off. Though the solubility of MCI in saline solution at elevated temperature is not great, it is desirable, in the interest of not losing as little MCI as possible, it is preferred to have a cool aqueous solution. If the reaction temperature is 65° C. the reaction mass need not be cooled in a heat exchanger further to decrease the solubility of the excess amine in the aqueous phase (saline solution), to force the excess amine (in solution) from the aqueous phase, into solution in the toluene phase. The particular low temperature to which the reaction mass is cooled is not critical, being determined by the cost of cooling versus the amount of amine saved, that is, forced back into toluene solution. A particularly economic temperature is to cool the reaction mass to about 65° C. at which temperature less than 2% by weight of the excess amine remains in aqueous solution, but the temperature is high enough to avoid having NaCl crystals separate from solution in the decantation tank.

It will be appreciated that the intermediate step may be carried out when using this staged process in a single reactor, after allowing the reaction mass to settle into two layers. Though so doing does not minimize the cost of a pressure reactor, it permits recycling the aqueous layer, if desired, as well as allowing precise determination of additional ingredients for addition to the reactor.

In the second sequence, the supernatant toluene solution is then pumped to a second reactor analogously equipped and configured as the first. For each mole of MCI, preferably from 1.2 to 1.4 moles, but no more than 1.5 moles of PSP, are added to the second reactor, along with preferably from 1.2 to 1.4 moles, but no more than 1.5 moles of aqueous base, so that there is just enough excess amine to make the third substitution within a predetermined time, and enough aqueous base to provide a concentration of at least 25% NaCl when at least 90% conversion of the MCI is obtained, preferably more than 95% conversion, but before the reaction mass begins to get very dark brown.

The reaction mass is then cooled down and allowed to settle so that the aqueous layer may be drawn off. The toluene solution is washed several times with water until substantially free from base, that is, having a pH of no more than 10. The water-washed toluene solution, preferably after being concentrated, is then dumped into a large excess of heptane, preferably a three- to four-fold excess or more, which causes the trisubstituted product crystals to be precipitated. These crystals are typically not free from color. They are dissolved in a suitable solvent, preferably toluene, with heating, and then recrystallized upon cooling.

An alternative novel method to refine the product is to wash the recovered toluene phase with copious quantities of water, then boil off a toluene/water azeotrope, meanwhile adding fresh water and boiling off further quantities of azeotrope, until only a water slurry of granules of product is left. The granules are then dissolved in an acetone/water mixture, refluxed, then cooled and filtered. Most of the color-forming impurities leave with the filtrate.

Since the higher the temperature and the more the water present, the greater the discoloration and loss of excess cyclic amine, it will now be evident that the reactor productivity will be optimized by balancing the cost of amine lost, against the time required to make an on-spec product, inter alia.

The prior art process is schematically illustrated in the block flow diagram FIG. 1 in which toluene or xylene 11, preferably toluene, or a mixture of toluene and xylene, is charged to a pressure-rated reactor 10 in an amount sufficient to form a solution of the cyanuric chloride 12 and the cyclic amine 13 which are added to the reactor. Enough 25% aqueous NaOH solution 14 is added so as to form a two-phase reaction mixture, the amount of NaOH being in a molar excess relative to the cyanuric chloride. The amount of cyclic amine (PSP) added is in the range from about 3 but less than 3.5 moles for each mole of said cyanuric chloride.

The reaction mixture is heated to, and maintained at, a temperature in the range from 125° C. but below 200° C., preferably from 150° C.–175° C., until at least 95% by weight of the cyanuric chloride, and preferably essentially all, is converted to the trisubstituted product. The conversion is determined by analysis for MCI remaining in the reaction mixture. When from about 1% to 2% MCI is detected, the mixture is pumped to wash tank 15 where it is allowed to settle, and the aqueous lower layer 16, drawn off. The remaining toluene layer is repeatedly washed with water in wash tank 15 until the pH of the wash water 16 is about 9 or less, typically 8-9 or 10. The washed toluene 17 is preferably concentrated, for example by stripping with steam in stripper 20, until a concentrate 21 which is somewhat viscous is obtained. The syrup 21 is mixed in precipitation tank 22 with a large excess of a liquid $C_6$–$C_{10}$ alkane 23, preferably heptane, and the precipitated solid product is removed. To improve the whiteness of the solid product, it is dissolved in fresh toluene or other suitable solvent, which is again stripped from the solution and the trisubstituted product recrystallized from it. The re-dissolving of the product may be done in the wash tank, and the remaining steps carried out in the same equipment used before.

Figure 2:
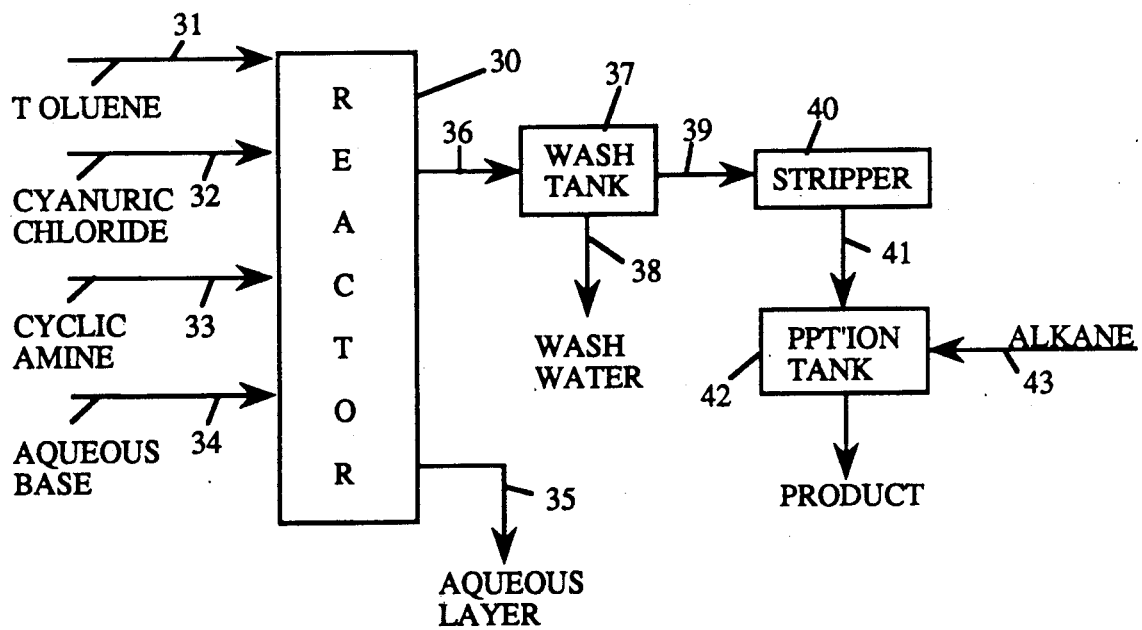
FIG. 2 is a block diagram schematically representing a flowsheet for the staged process of this invention using a single reactor in which the trisubstitution is effected in two sequences without withdrawing an aqueous layer of saline water in an intermediate step.

In a specific illustrative example of the prior art procedure, a molar ratio of 1 mol cyanuric chloride : 3.5 mols PSP:3.2 mols NaOH is charged to the reactor with enough toluene to have about 3 volumes of toluene for each volume of water. The reaction is carried out under a nitrogen blanket under autogenous pressure at 165° C. until from about to 2% MCI is detected in the reaction mixture, and the trisubstituted product was recovered as described above. The color of the product is marginally acceptable, but improves upon a subsequent recrystallization. No significant improvement in color is observed upon a third recrystallization. In a first embodiment of the staged process using a single reaction zone, less amine is used than in the prior art process. Referring to FIG. 2 there is diagrammatically shown a flowheet for a staged process using a single reactor 30 to which toluene 31, cyanuric chloride, cyclic amine 33 and aqueous base 34 are charged. The molar ratio of cyclic amine: cyanuric chloride: base is 2.2:1:2.3. The reaction is carried out at 65° C. under a nitrogen blanket and atmospheric pressure. Thereafter additional cyclic amine and base are added to provide a molar ratio of cyclic amine: cyanuric chloride: base=3.5:3:3.2, and the temperature raised to 165° C. The temperature is maintained until no cyanuric chloride is detected by a liquid chromatographic analysis. Thereafter, the reaction mass is cooled, allowed to settle, and the aqueous lower layer 35, drawn off. The remaining toluene layer 36 is repeatedly washed with water in wash tank 37 until the pH of the wash water 38 is about 10 or less. The washed toluene 39 is preferably concentrated, for example by stripping with steam in stripper 40, until the consistency of the concentrate 41 is perceptibly more viscous than before stripping. The concentrate 41 is mixed in precipitation tank 42 with a large excess of a liquid $C_6$-$C_{10}$ alkane 43, preferably heptane, and the precipitated solid product is removed.

Whiteness of the solid product may be improved by recrystallization from toluene as described hereinabove, or, by the novel process in which the colored product is boiled in a mixture of acetone and water.

Figure 3:
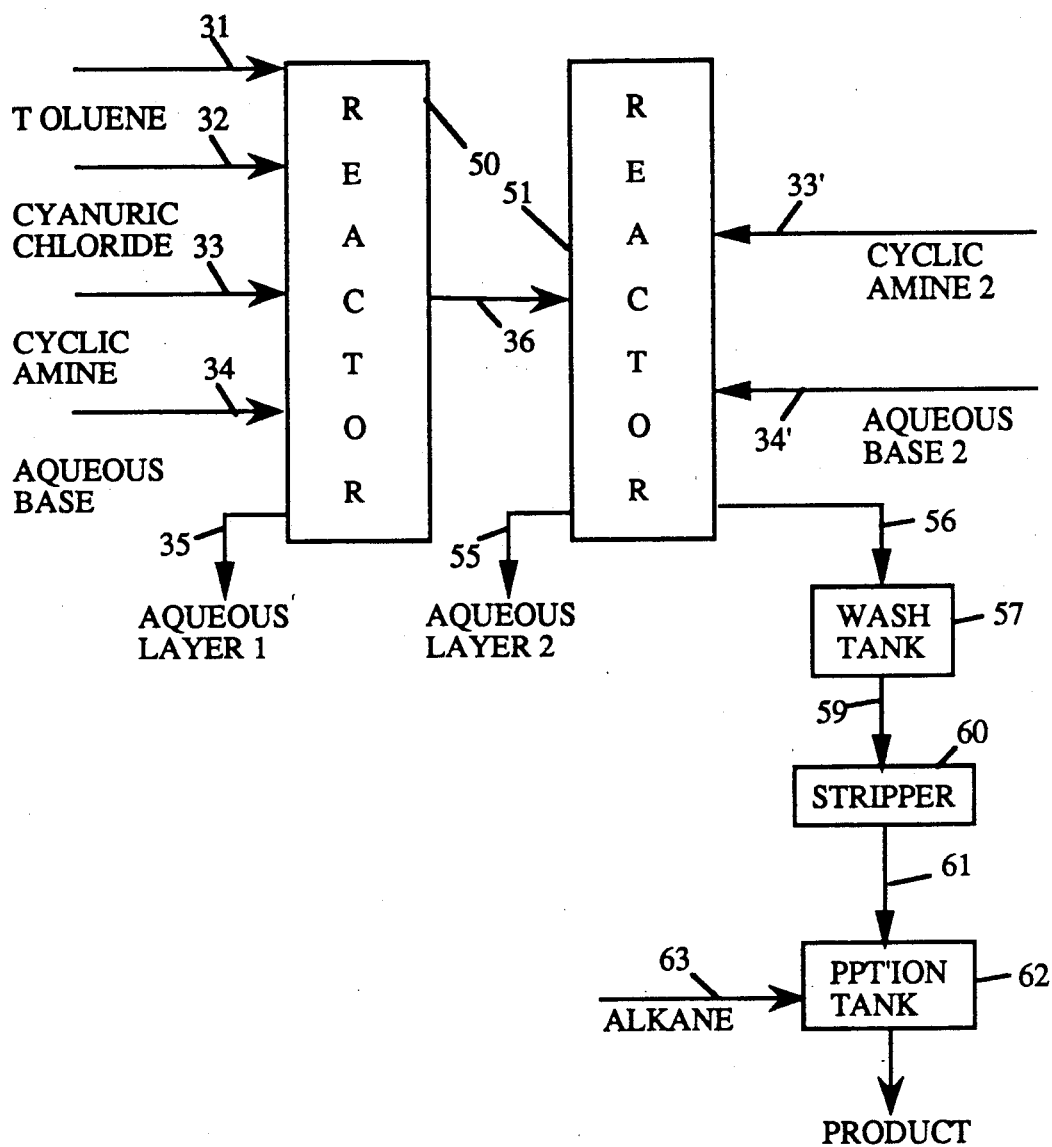
FIG. 3 is a block diagram schematically representing a flowsheet for the staged process of this invention using first and second reactors in which the first and second sequences, respectively, are carried out; and, an aqueous layer of saline water is withdrawn in an intermediate step.

In a second embodiment of the staged process using two, namely first and second reaction zones, less amine is also used than in the prior art process. Referring to FIG. 3 there is diagrammatically shown a flowheet for a staged process in which a first reactor 50 is charged with toluene 31, cyanuric chloride 32, cyclic amine 33 and aqueous base 34. The molar ratio of cyclic amine: cyanuric chloride: base is 2.2:1: 2.3 as before. The reaction is carried out at 65° C. under a nitrogen blanket and atmospheric pressure until complete. The lower aqueous saline layer 35 is then withdrawn and the remainder pumped as stream 36 to the second reactor 60.

The concentration of MCI in the stream 36 is measured and also the amount of excess cyclic amine. Enough additional cyclic amine 33' and base 34' are added so that the molar ratio of cyclic amine:MCI:base is 3.5:3:3.2 in reactor 51. The temperature is raised to 165° C. and maintained until from about 1% to 2% MCI is detected by a liquid chromatographic analysis. Thereafter, the reaction mass is cooled, allowed to settle, and the aqueous lower layer 55, drawn off. The remaining toluene layer 56 is repeatedly washed with water in wash tank 57 until the pH of the wash water is about 9. The washed toluene 59 is preferably concentrated, for example by stripping with steam in stripper 60, until a more viscous consistency of the concentrate 61 is achieved. The concentrate 61 is mixed in mixing tank 62 with a large excess of a liquid $C_6$-$C_{10}$ alkane 63, preferably heptane, and the precipitated solid product is removed. Whiteness of the solid product may be improved as described hereinbefore.

To determine the benefits of a staged process, a comparison of runs is made under the claimed conditions of the staged process, and, prior art conditions, namely a single sequence process. In each case, a sufficient excess of amine is added to a reaction zone to obtain at least 95% conversion of MCI and at least 90% yield of trisubstituted product.

Utilizing the same ratio of reactants, except using the staged process of our invention, upon recovery of the trisubstituted product from the precipitated solid, it was found in each case that the color was desirably white, being slightly off-white (melt absorptivity less than 3.5 mL/g.cm); and, the combined weight of byproducts formed in the first and second sequences is less than the weight of byproducts formed during the single sequence prior art process; further, the yield of product obtained in the staged process is higher than in the single sequence process.

The staged process is described hereunder in greater detail for a specific series of comparative runs in each of which the molar ratios of the reactants is maintained substantially the same.

In a first sequence, the cyanuric chloride is charged to the reactor containing enough toluene to form a solution; PSP is also charged, the amount of PSP being in the range from about 2.2 but no more than 3 moles of amine for each mole of cyanuric chloride; along with, at least a 30% aqueous solution of NaOH so as to form a two-phase reaction mixture in the reactor, the amount of NaOH being in a molar excess relative to the cyanuric chloride, but no more than 50% excess so as to maintain at least a volume ratio of toluene: water of at least 2.5; and, maintaining the reaction mixture at a temperature in the range from 20° C. to about 100° C. until at least 95% by weight, preferably all, of the cyanuric chloride is converted to MCI, forming a saline solution having a pH 14, and a concentration of at least 25% salt in the solution.

In the second sequence, an additional amount of PSP is charged to the reactor, the amount of PSP charged being in the range from about 3.2 but no more than 3.5 moles of amine for 3 moles of the MCI; in addition more NaOH solution is charged, the amount of NaOH being in a molar excess relative to the MCI, the molar excess being no more than 50% so as to maintain at least a volume ratio of toluene:water of at least 2.5. The reaction mixture is maintained at a temperature in the range from 125° C. but below 200° C., preferably forming a saline solution having a pH 14, and a concentration of at least 25% salt in the solution, until at least 95% by weight of the MCI is converted to triazine tri-substituted with PSP which is recovered from the reaction mixture in at least a 90% yield and 95% purity.

In each of the following examples J, K, L, M and N, for the overall reaction, the mole ratio of cyclic amine: cyanuric chloride:base is 3.5:1:3.2, and the corresponding weight (pounds) of each ingredient is used. In each case, the amounts of the ingredients are as follows: total amount of cyclic amine 1-[2-(cyclohexylamino)ethyl]3,3,5,5-tetramethyl-piperazin-2-one (985.1 lb); cyanuric chloride (184.4 lb); toluene (1000 lb); but the total amount of aqueous base (25% NaOH solution, i.e. 120 lb NaOH in 480 lb solution) may not be identical in each example.

EXAMPLE J

Prior Art Process

In this example of the prior art method, all ingredients are combined and heated to 165° C. in a single sequence reaction until there was substantially no MCI is detected in the reaction mass. The time for the reaction to be completed was 13 hr. Cooling of the reaction mass is immediately commenced, and the cooled mass allowed to settle. The aqueous layer is drawn off and the toluene layer washed five times to remove substantially all the base, then concentrated by stripping toluene. The concentrate is then dumped into heptane and the product crystals recovered. The cooled mixture is drawn off, leaving a product which is off-white, and has a melt absorptivity greater than 3.5 mL/gm.cm. The yield is less than 90% and there is no recoverable excess amine. The loss of unrecoverable product and the make of byproducts are together calculated by difference to be 12%.

EXAMPLE K

Stages Process—Single Reactor

In this example, the first and second sequences are carried out in the same reactor with no withdrawal of aqueous solution after the first sequence. 2.1 moles of the cyclic amine (590.5 lb), 1 mole of cyanuric chloride (184.4 lb) and 2.2 moles of 25% NaOH solution (88 lb NaOH in 352 lb solution) are combined in 1000 lb toluene and heated to 65° C. until there was substantially no cyanuric chloride detected in the reaction mass. An excess of NaOH is used so as to result, after the disubstitution with PSP is completed, in a concentration of at least 25% NaCl in the aqueous solution. The time for the reaction to be completed with about 98% yield of MCI which is held in solution, was 2 hr.

In the second sequence, 1.4 mole of cyclic amine is added along with 1 mole of 25% NaOH. The reaction mass is then heated to 165° C. and the temperature maintained until substantially no MCI is detected in the reaction mass. The time for completion of the reaction is 11 hr. Cooling of the reaction mass is immediately commenced, and the cooled mass allowed to settle. The aqueous layer is drawn off as before, and the toluene layer washed several times, until the basicity is about 9, as before. The toluene is then azeotroped off with sequential additions of water until granules of straw-colored product in a slurry are left. These granules are boiled in a mixture of equal parts by weight of acetone/water by refluxing the mixture, then cooled. The yield of trisubstituted product is about 92%. The melt absorptivity of the off-white crystals is 3 mL/gm.cm. The loss of unrecoverable product and the make of by-products are together calculated by difference to be 8%. Though there is no gain in the overall time required for the reaction, there is improvement in color.

EXAMPLE L

Staged Process—Two Reactors

In this example, the first sequence is carried out in a first reactor rated for operation at atmospheric pressure. The first sequence is carried out as in Example K. That is, 2.1 moles of the cyclic amine, 1 mole of cyanuric chloride and 2.2 moles of 25% NaOH solution are combined in 1000 lb toluene and heated to 65° C. until there was substantially no cyanuric chloride detected in the reaction mass. The time for the reaction to be completed with about 95% yield of MCI which is held in solution, was 2 hr.

About 500 lb of aqueous saline solution (pH 14) is withdrawn from the reactor, and the remaining toluene layer is pumped to the second reactor. The concentration of MCI, (conversion to MCI is in excess of 98%), and excess cyclic amine in the toluene layer is measured.

In the second sequence, carried out in a second reactor of smaller volume than the first and rated for operation at about 700 kPa (100 psia), 1.4 moles of cyclic amine are added to provide a total of 3.5 moles of cyclic amine for 3 moles of MCI. Also added is about 1.2 moles of 25% NaOH so as to result, after the reaction is completed, in a concentration of at least 25% NaCl in the aqueous solution. The reaction mass is then heated to 165° C. and the temperature maintained until less than 2% MCI, typically 1-2%, and more preferably substantially no MCI, is detected in the reaction mass. The time for completion of the reaction is 10 hr, the improvement being attributable to the smaller volume of aqueous phase present, compared to that in examples J and K.

Cooling of the reaction mass is immediately commenced, and the product worked up as in example K. The melt absorptivity of the off-white crystals is 3 mL/gm.cm. The yield of trisubstituted product is 92%. The loss of unrecoverable product and the make of by-products are together calculated by difference to be 8%. Though there is only a 9% gain in the time for completion of the trisubstitution in the second sequence, the time in the second reactor is only 10 hr compared with the overall 13 hr in the single sequence prior art process, or the dual sequence process using a single reactor. In addition to the gain in reactor productivity, there is a saving in cost of the second pressure reactor because of its smaller volume.

The Phase Transfer Catalyzed Dual Sequence Process

It was decided to use a phase transfer catalyst to determine if the reaction in the organic phase could be accelerated. The phase transfer catalyst used is not narrowly critical, and may be onium salts, macrocyclic polyether (crown ethers), macrobicyclic polyethers (cryptands), and the like, most preferred being the onium salts of a Group VA element of the Periodic Table having certain structural limitations. The preferred salts have the formula $R_nY^+X^-$ where Y is chosen from N, P and S; R represents either different or identical monovalent organic radicals bonded to Y by covalent linkages; $X^-$ is a counterion; and n is an integer which may be 3 or 4. When Y is pentavalent, for example P or N, then n=4, and when Y is tetravalent, for example S, then n=3. In an analogous manner, oniium salts having certain multivalent organic substituents may be useful in this invention. Examples include multivalent organic radicals that include Y in a ring, and those that are bonded to more than one Y.

More preferred onium salts for use in this invention have the formula $(R_aR_bR_cR_dY^+)X^-$ wherein Y is N or P, and $R_1$-$R_d$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The total number of carbon atoms in $R_a$, $R_b$, $R_c$, and $R_d$ if the salt is quaternary, should be at least 10 and is preferably in the range from about 15 to 40. No theoretical maximum number of carbon atoms for inclusion in the onium salts exists, although, in general, about 70 carbon atoms represents the upper limit imposed by practical limitations. Since the liquid phases involved are aqueous and organic, the number of carbon atoms and structure of the onium salts are usually selected to impart to the cyclic amine, the requisite solubiity in the organic phase, and relative insolubility in the aqueous phase. The onium salt is nonreactive to all materials in the reaction mixture except the reactants themselves, and the substitution of the PSP in the triazine takes place mainly in the organic phase.

Most preferred onium salts have Y=N, and the hydrocarbon radicals where $R_a$ is $C_2H_5$, and $R_b$, $R_c$, and $R_d$ are each selected from the group consisting of n-$C_4H_9$; n-$C_5H_{11}$; mixed $C_5H_{11}$; n-$C_6H_{13}$; mixed $C_6H_{13}$; $C_6H_5$; $C_6H_5CH_2$; n-$C_8H_{17}$; n-$C_{12}H_{25}$; n-$C_{18}H_{37}$; mixed $C_8$–$C_{10}$ alkyl; and the like. However, $R_a$ may also be selected from n-$C_3H_7$ and n-$C_4H_9$.

Various counterions may be used, including $Cl^-$, $Br^-$, $I^-$, $F^-$, $HSO_4^-$, and the like. Most preferred is $Cl^-$. A commercially available and highly effective onium salt is benzenetetraethylammonium chloride ("BTAC").

EXAMPLE M

Staged Phase Transfer Catalyzed

Single Reactor

In this example, the first and second sequences are carried out as described in Example K hereinabove, using the same amounts of ingredients, except that 2 phr (part by weight per 100 parts of reaction mixture), of BTAC is added to the reaction mass before commencing the first sequence, and an additional amount of BTAC, sufficient to maintain a 2 phr concentration, is added when additional amine and NaOH solution are added in the second sequence.

The time for completion of the reaction in the first sequence is 1.5 hr; and the time for completion of the reaction in the second sequence is 8 hr. The trisubstituted product is recovered as in example K. The yield is 90%. The loss of unrecoverable product and the make of by-products are together calculated by difference to be 7%.

EXAMPLE N

Staged Phase Transfer Catalyzed—Two Reactors

In this example, the first and second sequences are carried out in first and second reactors as described in Example L hereinabove, using the same amounts of ingredients, except that 2 phr of BTAC is added to the reaction mass before commencing the first sequence in the first reactor. The saline aqueous phase and some BTAC is withdrawn with the water, so an additional amount of BTAC, sufficient to provide 2 phr, is added when additional amine and NaOH solution are added in the second reactor.

The time for completion of the reaction in the first reactor is 1.5 hr; and the time for completion of the reaction in the second reactor is 7.5 hr. The trisubstituted product is recovered as in example K. The melt absorptivity of the off-white crystals is 3 mL/gm.cm. The yield of trisubstituted product is 90%. The loss of unrecoverable product and the make of by-products are together calculated by difference to be 7%. Thus, by using a second reactor and a phase transfer catalyst the time spent in the reactor is only 7.5 hr compared with 13 hr in a single sequence process.

Having thus provided a general discussion, and several specific illustrations of the best mode of operation of a dual sequence process for trisubstitution of a triazine ring with a polysubstituted cyclic amine, it is to be understood that no undue restrictions are to be imposed by reason thereof, except as provided by the following claims.

We claim:

1. A process for substituting each halogen of a trihalotriazine with a polysubstituted cyclic amine to make a trisubstituted triazine, said process comprising, in a first sequence,
    (a) charging said trihalo-s-triazine to a reaction zone containing enough alkylbenzene to form a solution of said trihalo-s-triazine;
    (b) charging said amine amine charged being in the range from more than 2 but less than 3 moles of amine for each mole of said triazine;
    (c) charging at least a 15% aqueous solution of inorganic base to said reaction zone so as to form a two-phase reaction mixture therewithin, the amount of said base being in a molar excess relative to said tri-halo-s-triazine, said molar excess being no more than 50% so as to maintain at least a volume ratio of alkylbenzene:water of at least 2.5; and,
    (d) maintaining said reaction mixture at a temperature in the range from 20° C. to about 100° C. until at least 95% by weight of said trihalo-s-triazine is converted to monochlorointermediate ("MCI"); and, in a second sequence,
    (e) charging an additional amount of said amine to said reaction zone, until the amount of amine in the reaction mixture is in the range from about 3.2 but no more than 3.5 moles of amine for 3 moles of said MCI,
    (f) charging an additional amount of said aqueous solution of inorganic base to said reaction zone in a concentration no greater than 50%, the amount of said base being in a molar excess relative to said MCI, said molar excess being no more than 50% so as to maintain at least a volume ratio of alkylbenzene:water of at least 2.5; and,
    (g) maintaining said reaction mixture at a temperature in the range from 125° C. but below 200° C. until at least 95% by weight of said MCI is converted to said tri-substituted triazine; and,
    (h) recovering said tri-substituted triazine from said reaction mixture in at least a 90% yield and 90% purity.

2. The process of claim 1 wherein said substituted triazine is represented by the structure

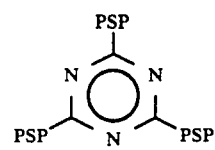

wherein PSP represents a substituent derived from a cyclic amine represented by a structure selected from the group consisting of

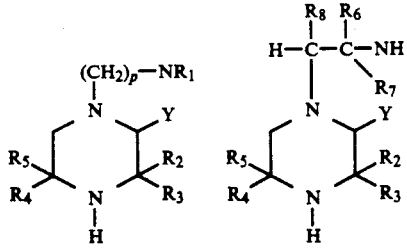

wherein,

Y represents H or =O, and m is 1 or 2;

$R_1$ represents $C_1$-$C_{24}$ alkyl, $C_5$-$C_{12}$ cycloalkyl, $C_7$-$C_{20}$ aralkyl or alkaryl, $C_1$-$C_{24}$ azaalkyl, $C_6$-$C_{20}$ azacycloalkyl;

$R_2$, $R_3$, $R_4$, and $R_5$ independently represent $C_1$-$C_{24}$ alkyl;

$R_6$, and $R_7$ independently represent $C_1$-$C_{24}$ alkyl and polymethylene having from 4 to 7 cyclizable carbon atoms;

p represents an integer in the range from 2 to 10; and, $R_8$ represents H, $C_1$-$C_6$ alkyl and phenyl; and,

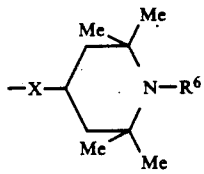

wherein,

Me=methyl, $R^6$ represents hydrogen, oxyl oxygen, $C_1$-$C_{12}$ alkyl, $C_3$-$C_7$ alkenyl, $C_1$-$C_{18}$ alkoxy, $C_7$-$C_{11}$ phenylalkyl, cyanomethyl, $C_2$-$C_{18}$ alkanoyl, $C_3$-$C_{18}$ alkenoyl, or a group —CON($R^7$)($R^8$) in which $R^7$ is $C_1$-$C_{12}$ alkyl, allyl, cyclohexyl, benzyl, phenyl, or $C_7$-$C_{12}$ alkylphenyl, and $R^8$ is hydrogen, $C_1$-$C_{12}$ alkyl, allyl or benzyl, or $R^7$ or $R^8$ together with the N atoms to which they are attached, form a 5-membered ring or 6-membered heterocylic ring; and X is a divalent group of the formula —O—, —NH—$CH_2$—$CH_2$—, —NH—$(CH_2)_2$—O— and the like; or a monovalent group of the formula RNH where R is $C_1$-$C_{18}$ alkyl or cycloalkyl; and,

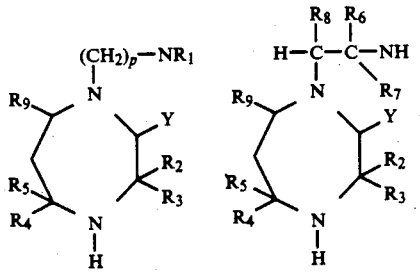

wherein, the substituents have the same connotation as given hereinabove, and, $R_9$ is $C_1$-$C_{12}$ alkyl.

3. The process of claim 2 wherein said tri-halo-s-triazine is cyanuric chloride, and step (d) includes forming a saline solution having a pH 14, and a concentration of at least 25% salt in said solution.

4. The process of claim 2 wherein said tri-halo-s-triazine is cyanuric chloride, and step (g) includes forming a saline solution having a pH 14, and a concentration of at least 25% salt in said solution.

5. The process of claim 2 including, in addition, boiling recovered solid product in a mixture of a acetone and water to improve the whiteness of said product.

6. The process of claim 5 wherein said PSP is represented by a structure (A) or (C), and said product has a melt absorptivity less than 3.5 mL/g.cm.

7. The process of claim 2 including, in said first sequence, charging a phase transfer catalyst in an amount in the range from about 0.1 part to about 5 parts per 100 parts of reaction mixture; and in said second sequence, charging said phase transfer catalyst until its concentration in said reaction mixture is in the range from about 0.1 part to about 5 parts per 100 parts of reaction mixture.

8. The process of claim 2 wherein in said first sequence, desired first and second amine substituents of said MCI may be the same or different; and, in said second sequence, reacting said MCI with a third amine, which may be the same or different from either one, or both, of the amine(s) used to provide the substituents of said MCI.

9. The process of claim 2 wherein in said first sequence, said triazine is connected through a tertiary N atom to a hindered amine substituent which may be the same or different on each C atom of said triazine.

10. The process of claim 7 including, in addition, boiling recovered solid product in a mixture of a acetone and water to improve the whiteness of the product.

11. The process of claim 9 wherein said PSP is (A) or (C).

12. A process for substituting each halogen of a trihalo-s-triazine with a polysubstituted cyclic amine to make a trisubstituted triazine, said process comprising, in a first sequence, (a) charging said trihalo-s-triazine to a first reaction zone containing enough alkylbenzene to form a solution of said trihalo-s-triazine;

(b) charging at least a 15% aqueous solution of inorganic amount of amine charged being in the range from more than 2 but less than 3 moles of amine for each mole of said triazine;

(c) charging at least a 15% aqueous solution of inorganic base to said reaction zone so as to form a two-phase reaction mixture therewithin, the amount of said base being in a molar excess relative to said tri-halo-s-triazine, said molar excess being no more than 50% so as to maintain at least a volume ratio of alkylbenzene:water of at least 2.5; and, (d) maintaining said reaction mixture at a temperature in the range from 20° C to about 100° C. until at least 95% by weight of said trihalo-s-triazine is converted to monochlorointermediate ("MCI"); in an intermediate step, (e) settling said reaction mixture and removing substantially all the aqueous saline solution; and, in a second sequence, (f) charging an additional amount of said amine to a second reaction zone, until the amount of amine in the reaction mixture is in the range from about 3.2 but no more than 3.5 moles of amine for 3 moles of said MCI, (g) charging an additional amount of said aqueous solution of inorganic base to said second reaction zone in a concentration no greater than 50%, the amount of said base being in a molar excess relative to said MCI, said molar excess being no more than 50% so as to maintain at least a volume ratio of alkylbenzene:water of at least 2.5;

(h) maintaining said reaction mixture at a temperature in the range from 125° C. but below 200° C. until at least 95% by weight of said MCI is converted to said tri-substituted triazine; and, (i) recovering said tri-substituted triazine from said reaction mixture in at least a 90% yield and 90% purity.

13. The process of claim 12 wherein said substituted triazine is represented by the structure

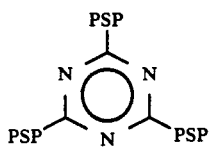

wherein PSP represents a substituent derived from a cyclic amine represented by a structure selected from the group consisting of

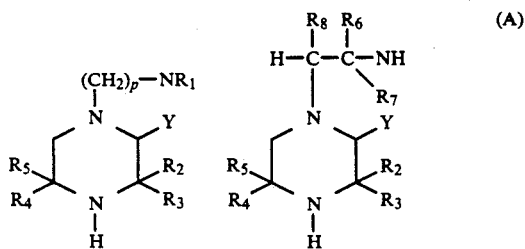

wherein,

Y represents H or =O, and m is 1 or 2;

$R_1$ represents $C_1$-$C_{24}$ alkyl, $C_5$-$C_{12}$ cycloalkyl, $C_7$-$C_{20}$ aralkyl or alkaryl, $C_1$-$C_{24}$ azaalkyl, $C_6$-$C_{20}$ azacycloalkyl;

$R_2$, $R_3$, $R_4$, and $R_5$ independently represent $C_1$-$C_{24}$ alkyl;

$R_6$, and $R_7$ independently represent $C_1$-$C_{24}$ alkyl and polymethylene having from 4 to 7 cyclizable carbon atoms;

p represents an integer in the range from 2 to 10; and, $R_8$ represents H, $C_1$-$C_6$ alkyl and phenyl; and,

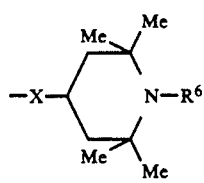

wherein,

Me=methyl, $R_6$ represents hydrogen, oxyl oxygen, $C_1$-$C_{12}$ alkyl, $C_3$-$C_7$ alkenyl, $C_1$-$C_{18}$ alkoxy, $C_7$-$C_{11}$ phenylalkyl, cyanomethyl, $C_2$-$C_{18}$ alkanoyl, $C_3$-$C_{18}$ alkenoyl, or a group —CON($R^7$)($R^8$) in which $R^7$ is $C_1$-$C_{12}$ alkyl, allyl, cyclohexyl, benzyl, phenyl, or $C_7$-$C_{12}$ alkylphenyl, and $R^8$ is hydrogen, $C_1$-$C_{12}$ alkyl, allyl or benzyl, or $R^7$ or $R^8$ together with the N atom to which they are attached, form a 5-membered ring or 6-membered heterocyclic ring; and, X is a divalent group of the formula —O—, —NH—$CH_2$—$CH_2$—, —NH—$(CH_2)_2$—O— and the like; or a monovalent group of the formula RNH where R is $C_1$-$C_{18}$ alkyl or cycloalkyl; and,

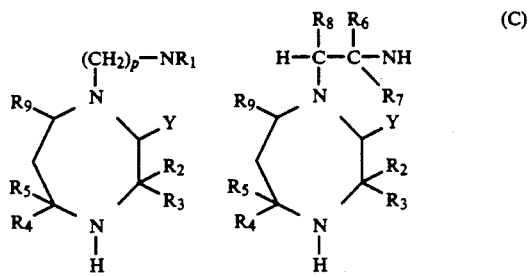

wherein, the substituents have the same connotation as given hereinabove, and, $R_9$ is $C_1$-$C_{12}$ alkyl.

14. The process of claim 13 wherein said tri-halo-s-triazine is cyanuric chloride, and step (d) includes forming a saline solution having a pH 14, and a concentration of at least 25% salt in said solution.

15. The process of claim 13 wherein said tri-halo-s-triazine is cyanuric chloride, and step (h) includes forming a saline solution having a pH 14, and a concentration of at least 25% salt in said solution.

16. The process of claim 13 wherein said tri-halo-s-triazine is cyanuric chloride, steps (d) and (h) each includes forming a saline solution having a pH 14, and a concentration of at least 25% salt in said solution.

17. The process of claim 13 including, in addition, boiling recovered solid product in a mixture of a acetone and water to improve the whiteness of said product.

18. The process of claim 16 wherein said PSP is represented by a structure (A) or (C), and said product has a melt absorptivity less than 3.5 mL/g.cm.

19. The process of claim 13 including, in said first sequence, charging a phase transfer catalyst in an amount in the range from about 0.1 part to about 5 parts per 100 parts of reaction mixture; and in said sequence, charging said phase transfer catalyst until its concentration in said reaction mixture is in the range from about 0.1 part to about 5 parts per 100 parts of reaction mixture.

20. The process of claim 13 wherein in said first sequence, desired first and second amine substituents of said MCI may be the same or different; and, in said second sequence, reacting said MCI with a third amine, which may be the same or different from either one, or both, of the amine(s) used to provide the substituents of said MCI.

21. The process of claim 13 wherein in said first sequence, said triazine is connected through a tertiary N atom to a hindered amine substituent which may be the same or different on each C atom of said triazine.

22. The process of claim 16 including, in addition, boiling recovered solid product in a mixture of a acetone and water to improve the whiteness of the product.

23. The process of claim 21 wherein said PSP is (A) or (C).

* * * * *